United States Patent
Shindelman et al.

(10) Patent No.: US 7,772,007 B2
(45) Date of Patent: Aug. 10, 2010

(54) ASSAY DEVICE FOR DIRECT MEASUREMENT OF LDL CHOLESTEROL

(75) Inventors: Jeffrey E. Shindelman, Castro Valley, CA (US); Thomas E. Worthy, Walnut Creek, CA (US); Ronald M. Jones, Mountain View, CA (US); George E. Withers, III, Livermore, CA (US)

(73) Assignee: Cholestech Corporation, Hayward, CA (US)

( * ) Notice: Subject to any disclaimer, the term of this patent is extended or adjusted under 35 U.S.C. 154(b) by 796 days.

(21) Appl. No.: 11/096,761

(22) Filed: Mar. 31, 2005

(65) Prior Publication Data

US 2005/0221502 A1   Oct. 6, 2005

Related U.S. Application Data

(60) Provisional application No. 60/559,382, filed on Apr. 2, 2004.

(51) Int. Cl.
G01N 33/92 (2006.01)
(52) U.S. Cl. .................. 436/71; 436/810; 436/824; 436/514; 436/518; 435/7.1; 435/11; 435/18; 435/25; 435/28; 435/805; 435/962; 422/56; 422/58; 422/73
(58) Field of Classification Search .................. 436/71, 436/810, 824, 514, 518; 435/7.1, 11, 19, 435/25, 28, 805, 962; 422/56, 58, 73
See application file for complete search history.

(56) References Cited

U.S. PATENT DOCUMENTS

| | | | |
|---|---|---|---|
| 4,746,605 A | 5/1988 | Kerscher et al. | |
| 5,135,716 A | 8/1992 | Thakore | |
| 5,286,626 A | 2/1994 | Law et al. | |
| 5,401,466 A | 3/1995 | Foltz et al. | |
| 5,407,836 A | 4/1995 | Ziegenhorn et al. | |
| 5,411,870 A | 5/1995 | Law et al. | |
| 5,426,030 A | 6/1995 | Rittersdorf et al. | |
| 5,580,743 A | 12/1996 | Rittersdorf et al. | |
| 5,786,164 A | 7/1998 | Rittersdorf et al. | |
| 6,107,045 A | 8/2000 | Koren et al. | |
| 6,171,849 B1 | 1/2001 | Rittersdorf et al. | |
| 6,214,570 B1 | 4/2001 | Rittersdorf et al. | |
| 6,844,149 B2 | 1/2005 | Goldman | |

(Continued)

FOREIGN PATENT DOCUMENTS

EP   0627627 A1   12/1994

(Continued)

OTHER PUBLICATIONS

International Search Report for International Application No. PCT/US05/11093, Oct. 24, 2005.

(Continued)

*Primary Examiner*—Bao-Thuy L Nguyen
(74) *Attorney, Agent, or Firm*—Wilson Sonsini Goodrich & Rosati, P.C.

(57) ABSTRACT

An assay device and method for measuring the concentration of LDL-associated cholesterol in a blood-fluid sample are described. The method employs selective precipitation of VLDL and chylomicrons and immunoseparation of HDL from a blood fluid sample. The assay device allows the assay to be performed entirely in a flow strip format.

7 Claims, 3 Drawing Sheets

U.S. PATENT DOCUMENTS 7,223,546 B2 * 5/2007 Miki et al. .................. 435/7.1

FOREIGN PATENT DOCUMENTS

| EP | 1028319 A2 | 8/2000 |
| EP | 1028319 A3 | 1/2004 |
| WO | WO 96/04556 A1 | 2/1996 |
| WO | WO 2004/025265 A2 | 3/2004 |
| WO | WO 2004/025265 A3 | 7/2004 |

OTHER PUBLICATIONS

Nauck, M. et al., "Analytical and clinical performance of a detergent-based homogeneous LDL-cholesterol assay: a multicenter evaluation", *Clin. Chem.* 46(4):506-514 (2000).

Paek, S.H. et al., "Immunochromatographic membrane strip assay system for a single-class plasma lipoprotein cholesterol, exemplified by high-density lipoprotein cholesterol measurement", *Biotechnology and Bioengineering* 62(2):145-154 (Jan. 1999).

McNamara, J.R. et al., "Immunoseparation for measuring low density lipoprotein cholesterol directly from serum evaluated", *Clin. Chem.* 41(2):232-240 (1995).

Sugiuchi, H. et al., "Homogeneous assay for measuring low-density lipoprotein cholesterol in serum with triblock copolymer and α-cyclodextrin sulfate", *Clin. Chem.* 44(3):522-531 (1998).

* cited by examiner

ASSAY DEVICE FOR DIRECT MEASUREMENT OF LDL CHOLESTEROL

This application claims priority to U.S. Provisional Application Ser. No. 60/559,382, filed Apr. 2, 2004, which is incorporated herein by reference in its entirety.

FIELD OF THE INVENTION

The present invention relates to a method of determining the concentration of low density lipoprotein (LDL)-associated cholesterol in a blood fluid sample, and a diagnostic assay device for carrying out the method.

REFERENCES

Cole, T. G., The role of immunochemistry in the direct measurement of low density lipoprotein cholesterol. *Journal of Clinical Ligand Assay* 19(3): 168-171 (1996).

Danczyk, R. et al., Comparison of Antibody Functionality Using Different Immobilization Methods. *Biotechnology and Bioengineering* 84(2):215-223 (2003).

Gromoll, B. et al., Methodologic studies of the isolation of VLDL using the lipoprotein precipitation reaction in the preparation of apolipoprotein E (Apo E). *Zeitschrift fur Medizinische Laboratoriumsdiagnostik* 30(8):445-9 (1989).

Kerscher, L. et al., Process and a reagent for the determination of low density lipoprotein (LDL). U.S. Pat. No. 4,746,605 (1988).

Law, W. T. et al., Process and apparatus for direct determination of low density lipoprotein. U.S. Pat. No. 5,411,870 (1995).

Law, W. T. et al., Process and apparatus for direct determination of low density lipoprotein. U.S. Pat. No. 5,286,626 (1994).

McNamara, J. R. et al., Immunoseparation for measuring low density lipoprotein cholesterol directly from serum evaluated. *Clin. Chem.* 41(2):232-240 (1995).

Nauck, M. et al., Analytical and clinical performance of a detergent-based homogeneous LDL-cholesterol assay: a multicenter evaluation. *Clin. Chem.* 46(4):506-514 (2000).

Paek, S. H. et al., Immunochromatographic membrane strip assay system for a single-class plasma lipoprotein cholesterol, exemplified by high-density lipoprotein cholesterol measurement. *Biotechnology and Bioengineering* 62(2): 145-154 (January 1999).

Kerscher, L. et al., Precipitation methods for the determination of LDL-cholesterol. *Clinical Biochemistry* 18(2): 118-25 (1985).

Sugiuchi, H. et al., Homogeneous assay for measuring low-density lipoprotein cholesterol in serum with triblock copolymer and α-cyclodextrin sulfate. *Clin. Chem.* 44(3): 522-531 (1998).

Utermann, G. et al., Polymorphism of apolipoprotein E. I. Methodological aspects and diagnosis of hyperlipoproteinemia type III without ultracentrifugation. *Clinical Genetics* 14(6):351-8 (December 1978).

Ziegenhorn, J. et al., Process and reagent for the determination of low density lipoprotein (LDL). U.S. Pat. No. 5,407,836 (1995).

BACKGROUND OF THE INVENTION

The amount of cholesterol present in the blood is known to be related to the risk of coronary artery disease. Cholesterol circulates in the blood predominantly in protein-bound form. The proteins which transport cholesterol are the lipoproteins, which are subdivided into classes based on their density. High-density lipoproteins (HDL), which typically account for about 20-30% of serum cholesterol, are involved in the catabolism of triglyceride-rich lipoproteins and in the removal of cholesterol from peripheral tissues and transport to the liver. The very-low density lipoproteins (VLDL) are triglyceride-rich lipoproteins which are synthesized in the liver and ultimately converted to low-density lipoproteins (LDL), which transport most of the plasma cholesterol in humans. Chylomicrons are a type of very low density lipoproteins that are synthesized in the intestinal mucosa and transport exogenous (dietary) cholesterol and triglycerides from the small intestine to muscle and adipose tissues. VLDL's typically account for about 5% of total serum cholesterol, while LDL's typically account for about 60-75%. However, diets high in saturated fat and cholesterol can cause an increase in the amount of LDL cholesterol in the blood.

A relationship between serum levels of different lipoproteins and risk of coronary disease has been established. In particular, if the proportion of serum cholesterol associated with LDL is high and/or the proportion associate with HDL is low, the risk of coronary disease is increased.

In view of the importance of relative serum cholesterol levels in risk assessment and management of atherogenic disease, considerable effort has been spent screening large populations of both normal and high-risk individuals for serum levels of HDL, LDL, as well as total cholesterol and triglycerides. The effectiveness of treatments of high-risk individuals has been monitored by regular testing of serum levels of cholesterol in the various lipoprotein compartments.

LDL-associated lipoprotein is often measured indirectly by separately determining total serum cholesterol, triglycerides, and HDL associated cholesterol. Various methods have been proposed for direct quantification of LDL. The different lipoproteins can be separated by ultracentrifugation, which is a generally accurate method for determining LDL, but impractical for clinical use. A series of patents by Ziegenhorn et al. (U.S. Pat. No. 4,746,605 (1988), U.S. Pat. No. 5,407,836 (1995), and U.S. Pat. No. 5,532,172 (1996)) describe a method in which HDL is removed from a serum sample by addition of an anti-HDL antibody, and triglyceride-rich very low density lipoproteins (VLDL) are removed by precipitation with an anionic polymer, e.g. dextran sulfate, leaving LDL in solution for independent quantification. However, this method requires manipulation of several solutions and typically employs centrifugation to remove the antibody-bound or precipitated lipoproteins.

Reports by Sugiuchi et al. (1998) and Nauck et al. (2000) describe a homogenous solution assay in which an anionic polymer, e.g. cyclodextrin sulfate, is used to reduce reactivity of VLDL and chylomicron cholesterol without precipitation, while a nonionic surfactant such as PEO/PPO is used to solubilize, and thus increase the reactivity of, cholesterol in LDL particles. The Direct LDL™ assay developed by Genzyme (see e.g. NcNamara et al., 1995; Cole, 1996) employs antibodies directed to VLDLs and HDLs to bind these lipoproteins, followed by centrifuging and filtering to recover the supernatant containing LDL.

These liquid-phase assays have a number of limitations with respect to their use in widespread screening. First, the methods generally require a venous blood sample, requiring a trained technician to draw, fractionate and aliquot the blood sample. The sample must be treated with reagents such as precipitating agent, binding agent, surfactant, and, in most cases, further processed to remove precipitated material. Although some of these procedures can be automated, analytical machines designed for this purpose are expensive and not widely available outside of large hospitals.

Law et al. (U.S. Pat. No. 5,411,870) describe a device for use in direct determination of LDL which does not require wet chemistry manipulation of the sample. However, the device requires a dissolvable layer which separates "LDL redissolution agents" from a zone containing soluble HDL and VLDL and precipitated LDL. The device relies on dissolution of the separating layer, which allows LDL in the first zone to be dissolved, after a time sufficient to allow HDL and VLDL in the first zone to be degraded by enzymes, and the hydrogen peroxide thereby generated to be consumed by catalase. It can be seen that timing of this dissolution would be critical to obtaining accurate quantification of LDL cholesterol.

It is therefore the object of the present invention to provide an LDL assay device and method which overcome the above-noted prior art disadvantages.

SUMMARY OF THE INVENTION

In one aspect, the invention provides an assay device for measuring serum cholesterol associated with low-density lipoproteins (LDL) in a blood fluid sample also containing high density lipoproteins (HDL), very low density lipoproteins (VLDL), and/or chylomicrons, the device comprising:

(i) a sample loading area, such as a sample well; and (ii) a plurality of porous elements through which the blood fluid sample can flow by capillary action and/or gravity, wherein adjacent elements are or can be placed in fluid communication with each other, the plurality comprising:

a VLDL/chylomicron precipitation element, containing reagents effective to selectively precipitate VLDL and chylomicrons in the sample, and composed of a material effective to remove such precipitated VLDL and chylomicrons from the sample;

an antibody element, containing an antibody effective to specifically bind HDL, thereby forming an HDL-antibody complex;

a capture zone, wherein the HDL-antibody complex can be bound and thereby removed from the fluid sample; and an LDL test pad, downstream of the capture zone and the precipitation element, in which LDL concentration can be assayed;

wherein the precipitation element is either upstream of the antibody element or downstream of the capture zone.

In one embodiment, the device further comprises, immediately downstream of the sample loading area, a sieving matrix effective to remove cells and other large particles from the fluid sample.

The antibody effective to specifically bind HDL is typically an anti-apolipoprotein A1 or A2 antibody, preferably a monoclonal antibody.

In a preferred embodiment of the device, the antibody element contains, in soluble form, a conjugate of a binding agent, such as biotin, with the antibody, and the capture zone contains an immobilized capture agent, such as avidin, is adjacent and downstream of the antibody element, and can be placed in fluid communication with the antibody element. In this embodiment, the antibody element is also referred to as a "conjugate pad".

In another embodiment of the device, the antibody element and the capture zone are provided in the form of an element containing the antibody in immobilized form In this case, the steps of "placing the sample in fluid communication with the antibody element" and "contacting the HDL-antibody complex (formed therein) with the capture zone" both occur within this element.

The device preferably includes mounting means effective to adjust the relative positions of the porous elements in such a way as to bring elements into or out of fluid communication with each other. For example, the mounting means can be effective to bring the antibody element (conjugate pad) into fluid communication with the capture zone, when they are provided as separate elements. The device may comprise, in this respect, a porous bridging element which can be brought into simultaneous contact with the antibody element (conjugate pad) and the capture zone.

The mounting means can also be used to bring the LDL test pad into or out of fluid communication with either the capture zone or the precipitation element, whichever is further downstream When the device is designed to initially remove VLDL from the sample, the capture zone, further downstream; when it is designed to initially remove HDL from the sample, the precipitation element is further downstream.

In a related aspect, the invention provides a method of directly measuring low-density lipoproteins (LDL) in a blood fluid sample also containing high density lipoproteins (HDL), very low density lipoproteins (VLDL), and/or chylomicrons, by passing the sample through a plurality of porous elements in sequence, the method comprising:

(i) sequentially removing VLDL/chylomicrons and HDL from the sample, in either order, wherein removing VLDL/chylomicrons comprises: passing the sample through a VLDL/chylomicron precipitation element, containing reagents which selectively precipitate VLDL and chylomicrons in the sample and composed of a material which removes such precipitated VLDL and chylonicrons from the sample;

and wherein removing HDL comprises: passing the sample through an antibody element, containing an antibody effective to specifically bind HDL in the fluid sample, thereby forming an HDL-antibody complex, and contacting the HDL-antibody complex with a capture zone, wherein the HDL-antibody complex is bound and thereby removed from the fluid sample; and (ii) subsequently passing the sample into an LDL test pad, in which the LDL concentration of the sample is assayed.

In a preferred embodiment of the method, the antibody element contains, in soluble form, a conjugate of a binding agent, such as biotin, with the antibody, and the capture zone contains an immobilized capture agent, such as avidin, is adjacent and downstream of the antibody element, and can be placed in fluid communication with the antibody element. Alternatively, the antibody element and the capture zone can be provided in the form of an element containing the antibody in immobilized form In the latter case, the steps of "placing the sample in fluid communication with the antibody element" and "contacting the HDL-antibody complex (formed therein) with the capture zone" both occur within this element.

The method may employ initial removal of VLDL/chylomicrons from the sample, and would thereby comprise the steps of:

(a) placing the sample in fluid communication with the VLDL/chylomicron precipitation element;

(b) maintaining or placing the precipitation element in fluid communication with the antibody element, wherein the HDL-antibody complex is formed;

(c) contacting the HDL-antibody complex with the capture zone; and (d) placing the capture zone in fluid communication with the LDL test pad.

Alternatively, the method may employ initial removal of HDL from the sample, and would thereby comprise the steps of:

(a) placing the sample in fluid communication with the antibody element, wherein the HDL-antibody complex is formed;

(b) contacting the HDL-antibody complex with the capture zone;

(c) maintaining or placing the capture zone in fluid communication with the VLDL/chylomicron precipitation element;

(d) placing the precipitation element in fluid communication with the LDL test pad.

Preferably, the method further comprises, prior to these steps, passing the fluid sample through a sieving matrix effective to remove cells and other large particles from the sample. The method also preferably comprises, following these steps, breaking the fluid communication between the capture zone (or the precipitation element) and the LDL test pad, when a desired amount of fluid sample has been transferred.

These and other objects and features of the invention will become more fully apparent when the following detailed description of the invention is read in conjunction with the accompanying drawings.

DETAILED DESCRIPTION OF THE INVENTION

I. Definitions

The terms below have the following meanings unless indicated otherwise.

A first element is in "fluid communication" with a second element when a fluid is able to travel from the first to the second element, via a path of contiguous solid elements, under the impetus of capillary action and/or gravity. The first and second elements may be in direct contact, or elements through which the fluid can pass may be intervening, as long as the first and second elements are connected by a contiguous path of solid elements. Generally, these intervening elements are not reagent-containing elements (as defined below).

An element is "not in fluid communication" with another element when a fluid is not able to travel from one element to the other via capillary action and/or gravity. Typically, the elements are physically separated, i.e. spaced apart and/or separated by a region that does not transport fluid.

Two elements in an assay device which are "adjacent" are positioned such that, during the assay procedure, sample flows from one to the other without contacting any intervening reagent-containing element.

"Reagent-containing" refers to reagent initially present in an element, e.g. by impregnation or immobilization, and not to reagent that might be introduced by sample flowing into the element.

A "pad", such as a reagent pad or assay pad, as used herein, may comprise any material, such as a porous membrane or fibrous strip, which can contain impregnated or immobilized reagents and through which fluid can move via capillary action and/or gravity.

II. Assay Device

Figure 1A:
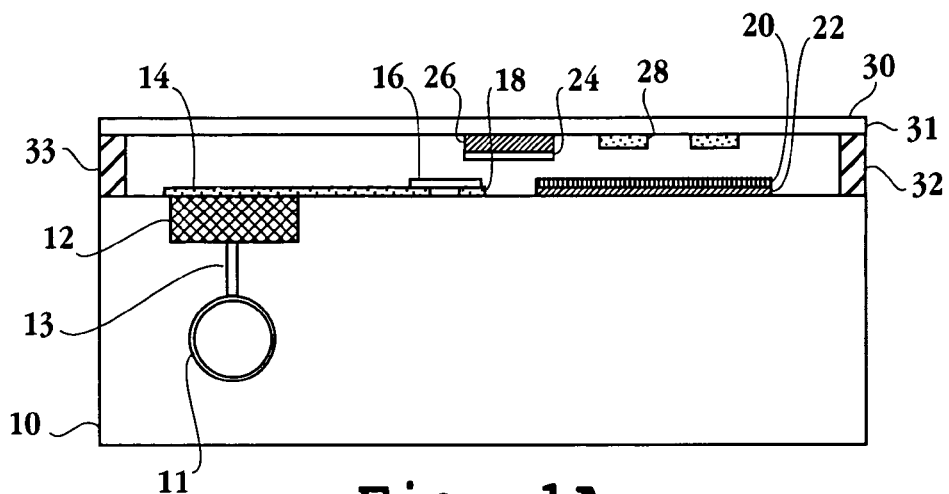
FIGS. 1A-C are side views of an exemplary assay device, constructed in accordance with one embodiment of the invention, employing a soluble antibody region, at different stages of an assay procedure.

FIG. 1A illustrates one embodiment of an assay device constructed in accordance with the present invention. The device is designed particularly for determining serum cholesterol associated with LDL (also referred to as LDL-associated cholesterol or simply LDL cholesterol) using a small volume of blood sample, typically between 10-50 µl of blood. The determination is carried out in a flow strip format, without the need for manipulation of solutions, and is amenable to automation.

The apparatus includes a main body or support 10 which defines a sample loading area, such as well 11, dimensioned and sized to receive a quantity of a blood sample, typically between about 10-50 µl. In one embodiment, as illustrated in FIG. 1A, the well is in fluid communication with a sieving pad 12, which may be carried in a notched region formed in the upper edge of the support. The fluid communication may be by direct contact, or, as in the device shown in FIG. 1A, provided by a capillary conduit 13 formed in the plate at the base of the well. The support is preferably a plastic plate, with the sample loading area, notched region and/or capillary formed by standard molding or machining methods.

Sieving pad 12 functions to remove large particulate matter (including blood cells) as the sample migrates through the pad matrix in a bottom-to-top direction as shown in the figure. Pad 12 is preferably formed of a glass fibrous matrix of material designed to draw aqueous fluid by surface wetting, and to retard the movement of blood cells as the blood sample is drawn through the matrix. One exemplary pad is a glass fiber filter, such as a GF/D or PD008 filter supplied by Whatman, having a packing density of about 0.16 g/cm$^3$, and a thickness of about 1 mm. The pad is dimensioned to absorb a defined volume of sample fluid, preferably between about 15-25 µl. Sieving pad 12 may additionally contain red blood cell capture reagents, such as lectins, antibodies specific for red blood cell surface membrane proteins, thrombin, or ion exchange agents.

A. General Description Employing Initial Removal of VLDL

Figure 1B:
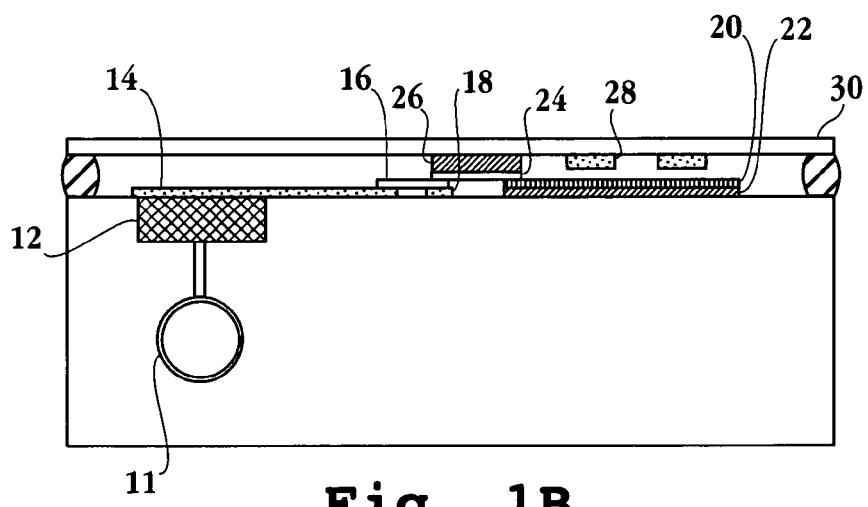
Figure 1C:
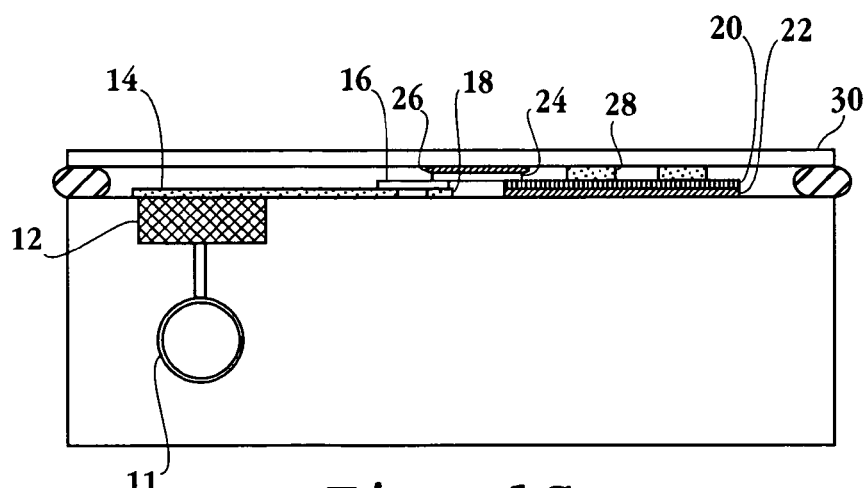

In the embodiment shown in FIGS. 1A-C, the sieving pad 12 contacts a porous elongate strip 14 which extends partially along the upper edge of plate 15. This strip, referred to as a VLDL precipitation strip, element, or region, contains reagents effective to selectively precipitate VLDL and chylomicrons from the blood fluid sample; the precipitated particles are removed from the fluid by filtration.

The strip is preferably a glass fiber filter having a packing density and thickness effective to absorb the volume of sample fluid, e.g., 10-25 µl, supplied to the strip. A preferred packing density is between about 0.16 g/cm$^3$ and 4.0 g/cm$^3$. This strip may also be supported by foam cushions or other supports (not shown), as long as it is in fluid communication with pad 12.

Figure 2:
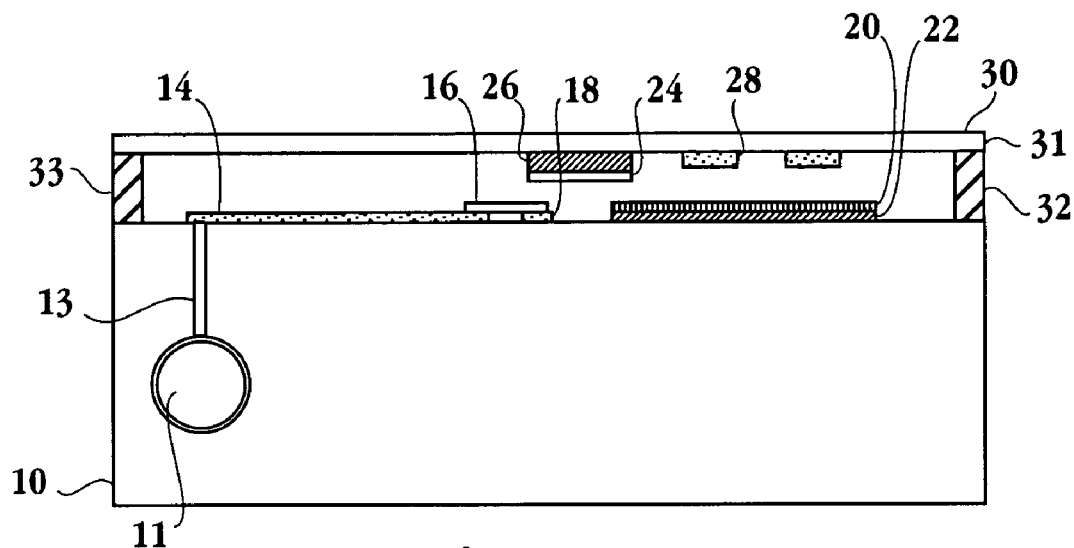
FIG. 2 is a side view of another embodiment of the assay device of FIG. 1A.

In another embodiment of the device, shown in FIG. 2, the sieving function, for removal of blood cells and other large particles, is incorporated into element 14, such that a separate sieving pad 12 is not included. In this case, element 14 is in fluid communication with well 11, either directly or via a conduit such as 13.

As noted above, element 14 contains reagents effective to selectively precipitate VLDL and chylomicrons from the blood fluid sample. Reagent systems effective to selectively precipitate VLDL and chylomicrons from a serum sample, i.e. without significant precipitation of LDL, are known in the art. Such reagents include sulfonated polysaccharides, heparin, and phosphotungstate, in the presence or absence of a group II cation, such as $Mg^{2+}$, $Mn^{2+}$, or $Ca^{2+}$. Selective VLDL precipitation has been described using, for example, phosphotungstic acid/$MgCl_2$ (see H. Schriewer et al., *J. Clin. Chem. & Clin. Biochem.* 22(1):35-40, 1984), heparin/$MnCl_2$ (see S. M. Lamplugh et al., *Clinica chimica acta* 86(1):31-6, 1978), heparin/$MgCl_2$ (see Uterman et al., Gromoll et al., both cited above), and dextran sulfate/$CaCl_2$ (see Kerscher et al., cited above). In general, a lower concentration of reagent is used than would be used to precipitate VLDL and LDL together. The effectiveness of a particular reagent system and concentration can be determined using methods known in the art.

For example, a precipitation reagent containing 130 mM MgOAc and 0.15% heparin was found to precipitate the majority of VLDL/chylomicrons from a serum sample without precipitating significant amounts of LDL. Precipitation of VLDL/chylomicrons was assessed by measuring triglycerides in the sample before and after exposure to the reagent. To determine retention of LDL in the sample, LDL in the precipitated sample was determined conventionally, by subtracting HDL from total cholesterol, and compared with starting LDL levels that had been determined on a Beckman Synchron analyzer.

Methods of immobilizing such precipitation reagents on a polymeric substrate are described in co-owned U.S. Appn. Pubn. No. 2003/0224471, which is incorporated herein by reference. In general, however, the precipitation reagents can be simply applied in solution and dried onto the strip for preparation of the precipitation element.

Adjacent the VLDL precipitation element, in one embodiment of the invention, is a conjugate pad 16. The pad may be elevated relative to the precipitation element, as shown in FIG. 1A. It may be in continuous fluid communication with the element 14, as shown in the figure, or the assay device may be constructed such that these two elements can be brought into fluid communication after the blood fluid sample has permeated VLDL precipitation element 14. The conjugate pad is typically a porous polymeric material (e.g. polyethylene, polypropylene, nylon, polysulfone), such as provided by Porex Corporation. It is preferably supported by a foam support as shown at 18.

In accordance with one embodiment of the invention, the conjugate pad 16 contains, in soluble form, an antibody-binding agent conjugate, specifically, a conjugate of a binding agent with an antibody effective to specifically bind a component of HDL, such as apolipoprotein A1 or A2. The antibody is preferably a monoclonal antibody, but a polyclonal antibody may also be used. By "soluble form" is meant that the binding agent-antibody conjugate is not immobilized to the conjugate pad material.

The binding agent component of the conjugate is one member of a binding pair, where the other member may be referred to as a "capture agent". Examples of such binding pairs include biotin/avidin or streptavidin, enzyme/substrate, lectin/carbohydrate, base-paired nucleic acids, DNA binding protein/DNA binding site, hormone/receptor, antigen/antibody, and protein A/immunoglobulin. In a preferred embodiment, the binding agent is biotin.

In accordance with the embodiment shown in FIGS. 1A-C, fluid sample from which VLDL and chylomicrons have been removed, in element 14, flows to conjugate pad 16, wherein HDL present in the fluid sample binds with the soluble binding agent-antibody conjugate, forming a soluble HDL-antibody-binding agent complex (e.g., an HDL-apo A1 antibody-biotin complex or an HDL-apo A2 antibody-biotin complex).

Various methods exist for modification and conjugation of antibodies; see, for example, *Bioconjugate Techniques*, G. T. Hermanson, Academic Press, 1996. In particular, antibodies can be readily biotinylated using, for example, reagent kits available from Pierce Biotechnology, Rockford, Ill. For example, the EZ-Link™ Sulfo-NHS-LC-Biotinylation Kit includes biotinylation reagent (sulfo-NHS-LC-biotin), PBS buffer mix, a desalting column, and reagents for use in determining moles of conjugated biotin/antibody in the product. Typically, 3-6 biotin molecules are conjugated to each antibody molecule, via lysine side chains.

Monoclonal antibodies can be produced from hybridoma cells by well known methods, e.g. according to the standard techniques of Köhler and Milstein, *Nature* 265:495-497, 1975. Reviews of monoclonal antibody techniques are found in *Lymphocyte Hybridomas*, ed. Melchers et al., Springer-Verlag (New York 1978); *Nature* 266: 495 (1977); *Science* 208: 692 (1980), and *Methods of Enzymology* 73 (Part B): 3-46 (1981). Various conventional methods exist for isolation and purification of monoclonal antibodies from other proteins and other contaminants (see Köhler and Milstein, supra). In general, antibodies can be purified by known techniques such as chromatography, e.g., DEAE chromatography, ABx chromatography, and the like, filtration, and so forth.

Monoclonal antibodies to apolipoprotein A1 or apolipoprotein A2 (as well as polyclonal antibodies) can also be obtained commercially from various suppliers of antibodies, such as, for example, Intracel Resources LLC, Frederick, Md.; Fitzgerald Industries International Inc, Concord, Mass.; and other Zymed Laboratories, Inc., South San Francisco, Calif.; Pierce Biotechnology, Rockland, Ill.; Abcam, Cambridge Science Park, UK; Serotec, Raleigh, N.C.; and Dako-Cytomation, Denmark.

In one embodiment of the device, a capture zone 20 is located adjacent the conjugate pad, but spaced apart from the pad, as shown in FIG. 1A. This region comprises a porous absorbent material through which fluid may flow by capillary action and on which a second member of a binding pair, or capture agent, effective to bind to the binding agent described above, is bound or immobilized. As noted above, examples of such binding pairs (with members listed in arbitrary order) include biotin/avidin or streptavidin, enzyme/substrate, lectin/carbohydrate, base-paired nucleic acids, DNA binding protein/DNA binding site, hormone/receptor, antigen/antibody, and protein A/immunoglobulin. The second member of the binding pair (capture agent) is bound or immobilized to the capture zone using known bioconjugation techniques, such as described, for example, in Hermanson, cited above.

In a preferred embodiment, where the binding agent is biotin, the capture agent is avidin or streptavidin. The capture zone may then be prepared by suspending avidin coated beads, such as are available from Bangs Laboratories, Inc., in glass fiber material, or by direct immobilization of avidin on nitrocellulose, using known methods. For example, a streptavidin or avidin solution (e.g. 10 mg/mL avidin in 0.1 M phosphate buffer at pH 7) is spray coated onto a nitrocellulose membrane, which is then dried at 50° C. for about 5 minutes. If desired, the membrane can then be treated with a blocking solution, followed by drying under vacuum, to block the residual binding capacity of the membrane and prevent non-specific binding. Blocking reagents typically include proteins, synthetic polymers, and/or surfactants which do not specifically bind assay components.

The capture agent (e.g. avidin) in capture zone 20 removes binding agent-containing materials, e.g. biotin-antibody-HDL complex formed in conjugate pad 16, from fluid sample within this region. Accordingly, capture zone 20 includes sample in which the only soluble lipoprotein present in significant quantities is LDL. Studies in support of the invention showed that avidin on beads or on nitrocellulose efficiently removed biotinylated anti-ApoA1 antibody-HDL complex from sample fluid.

Preferred materials for the capture zone include porous, fused polymer or microporous polymer membranes, such as polysulfone, polypropylene, nylon, nitrocellulose, Teflon®, or polyvinylchloride microporous membranes. In the present case, nitrocellulose, such as is available from Millipore, is particularly preferred. The nitrocellulose or other absorbent material may be cast onto a sheet of clear Mylar® or similar material. It is preferably supported on a foam support 22 which places its upper surface at substantially the same height within the device as the upper surface of precipitation element 14.

The device also includes at least one wettable, absorbent reaction test pad which, in the embodiment shown in FIGS. 1A-C, can be placed in contact with the capture zone 20 (or with a further downstream element into which sample flows from capture zone 20). Preferably, the device includes a reaction bar 30 composed of an elongate support 31 and a test pad, such as shown at 28, carried on the lower surface of the support, as shown in FIG. 1A.

Each test pad used in a particular assay contains analyte-dependent reagents effective to produce an analyte-dependent change in the pad which can be detected in a known manner, as described further below. All or any integral subset of the test pads may be employed in a particular assay. At least one test pad, e.g. test pad 28, contains reagents, such as described below, effective to assay the concentration of LDL in the blood fluid sample which enters the test pad.

The reaction test pads are preferably porous polymer membranes, typically having a thickness of about 100-150 μm and side dimensions of about 3 mm. (Relative thickness of test pads in FIG. 1 has been exaggerated for the sake of illustration.) The absorption volume of each pad is preferably between about 0.5-1.0 μl. The reaction pads may be asymmetric membranes; that is, membranes having a porosity gradient across the thickness of the membrane. In this case, the smaller pored side of the membrane preferably faces upward, such that this side is observed for detection.

Support 31 is either transparent or has window (not shown) on its upper surface which allow the test pads to be viewed through the upper surface of the support. These windows may be transparent materials or simply openings in the support. The reaction test pads in the reaction bar are attached to the support by standard methods, e.g. via a transparent or translucent adhesive material, or by sonic welding or other suitable bonding method.

The device also provides means for establishing fluid communication between conjugate pad 16 and capture zone 20, when these are provided as separate elements. In one embodiment, as shown in FIG. 1A, a bridging pad 24 is provided which can be brought into mutual contact with the above-referenced elements (as shown in FIG. 1B). In the embodiment shown in FIG. 1, the bridging pad is attached to reaction support bar 31. In this embodiment, a compressible support pad 26 is provided having sufficient thickness such that pad 24 can be placed in contact with region 20 without placing test pad 28 in contact with region 20. Support pad 26 is sufficiently compressible such that, in a later stage of the assay, as shown in FIG. 1C, test pad 28 can be placed in contact with region 20 (or with a further downstream element into which sample flows from capture zone 20). Support pad 26 is typically a foam support but can be any compressible and resilient material or element.

In the embodiment of FIGS. 1A-C, the reaction bar 30 is mounted on support 10 by mounting means effective to adjust the relative positions of the support and the reaction bar, and thereby adjust the relative positions of the above-described elements mounted on the support and reaction bar.

The mounting means can include, for example, a pair of resilient members, such as blocks 32, 33. By compression or release of the resilient members, fluid communication between the above-described elements can be selectively established and separated. Specifically, the mounting means act to establish fluid communication between bridging pad 26 and capture zone 20, and, in a later stage of the assay, between the test pad 28 and capture zone 20 (or a further downstream element into which sample flows from capture zone 20). The fluid communication may be via direct contact or through an intermediate element.

The mounting means can also be used to discontinue fluid communication between the elements, such as between capture zone 20 and test pad 28 after a desired amount of sample has been transferred to test pad 28, and/or after a desired contact time. This can be accomplished by release of resilient members 32, 33. The transfer time can be controlled automatically by monitoring the reflectance at the top surface of the test pad, which reflects extent of wetting, as described in co-owned U.S. Pat. No. 5,114,350. Alternatively, when the absorption capacity and rate of sample uptake of the pad material are known, the quantity of sample can be controlled with sufficient accuracy simply by using a predetermined contact time.

The support blocks 32, 33 are typically elastomeric or foam supports but can comprise any compressible and resilient material or element. They can be compressed and released by means of springs or a piston-like action. Alternatively, external mechanical devices could engage the support 10 and/or reaction bar 30 and move one towards the other. Such devices may include conventional components such as clamps, pistons, stepper motors, worm gears, or the like. An exemplary system is the Cholestech LDX® Analyzer, a self-contained, automated analyzer advantageous for use with assay devices such as described herein.

Test pad 28 contains reagents for assaying LDL level, as known in the art, in the sample fluid therein. Preferably, these reagents include cholesterol esterase, for releasing free cholesterol from the lipoprotein, cholesterol oxidase, for producing $H_2O_2$ by reaction with free cholesterol, peroxidase, and a coupled dye system which is converted, in the presence of peroxidase and $H_2O_2$, to a distinctively colored signal reaction product. Evolved $H_2O_2$ can also be measured by a biosensor, as described, for example, in co-owned U.S. Appn. Pubn. No. 2003/0224471 and in PCT Pubn. No. WO 99/58966 (Dobson et al.), which are incorporated herein by reference.

If desired, selected assay reagents, e.g. peroxidase, may be immobilized to the test pad membrane, according to well known methods for enzyme immobilization. (See e.g. U.S. Pat. No. 4,999,287; U.S. Pat. No. 5,419,902; Blum, L. J. et al., *Anal. Lett.* 20(2):317-326 (1987); Kiang, S. W. et al., *Clin. Chem.* 22(8):1378-82 (1976); Guilbault, G. G., Ed., *Modern*

*Monographs in Analytical Chemistry, Vol. 2: Analytical Uses of Immobilized Enzymes* (1984); Torchilin, V. P., *Progress in Clinical Biochemistry and Medicine, Vol. 11: Immobilized Enzymes in Medicine* (1991).)

Other arrangements of the above-described elements could be devised such that fluid communication between the elements could be established or discontinued as described. As noted above, fluid communication may be by direct contact or through an intermediate element. For example, a capture zone element could be supported, e.g. by a compressible support pad or other support, in a substantially coplanar position between the LDL test pad 28 and the conjugate pad 16.

B. Alternative Design Employing Initial Removal of HDL

Figure 4:
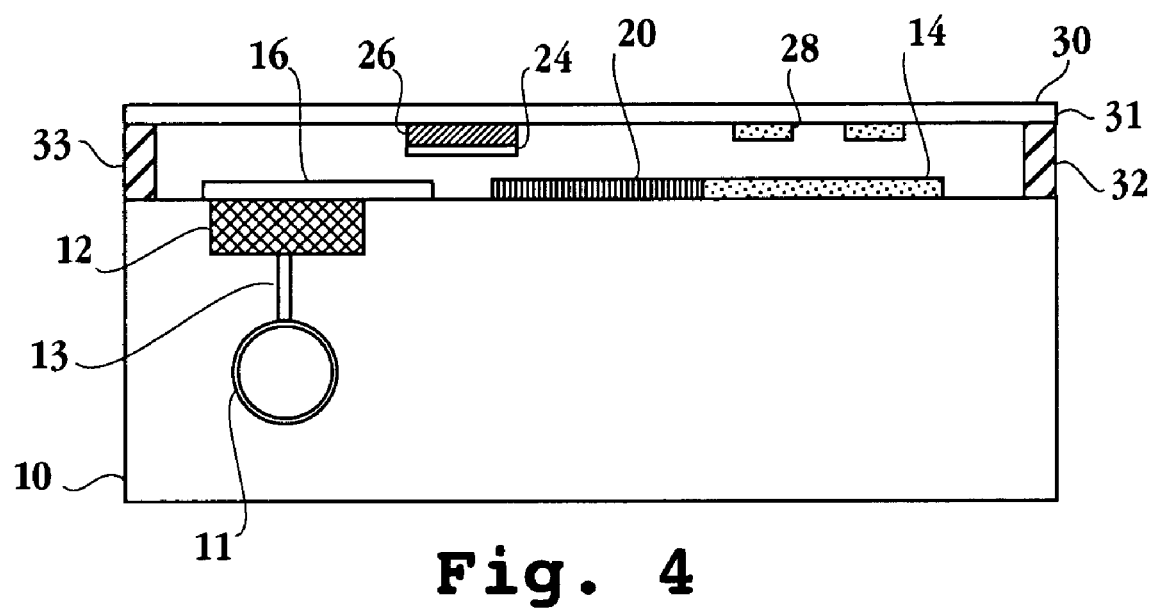
FIG. 4 is a side view of a further embodiment of the assay device, in which the order of removal of sample components is altered.

In an alternative embodiment, the device can be designed, as shown in FIG. 4, such that HDL is first removed from the fluid sample, followed by removal of VLDL/chylomicrons. In this embodiment, conjugate pad 16, rather than precipitation element 14, is adjacent the sample loading area, and is or can be placed in fluid communication with the sample loading area, either directly or via sieving pad 12. As described for the embodiment of FIG. 1A, capture zone 20 is located adjacent and spaced apart from the conjugate pad, and the device includes means for placing these two elements in fluid communication, either directly or via a bridging element, such as 24. In this embodiment, the precipitation element 14, for removal of VLDL/chylomicrons, is in a downstream position from the capture zone. The precipitation element is or can be placed in fluid communication with the capture zone.

As in the embodiment shown in FIG. 1A, described above, the device of this embodiment includes at least one wettable, absorbent reaction test pad, such as 28, which may be mounted on a reaction bar 30. In this embodiment, the elements are positioned such that test pad 28 can be placed in contact with the precipitation element 14, or with a further downstream element into which sample flows from the precipitation element. Contact between the elements can be initiated and/or broken by a process analogous to that shown in FIGS. 1B-C.

C. Alternative Design Employing Immobilized Antibody

In another variation on the basic design of the assay device, which may be applied to any of the embodiments described above, the anti-HDL antibody (e.g. anti-apoA1 antibody) can be immobilized to a capture zone, rather than employed in soluble form. Methods of immobilizing antibodies and other proteins to various substrates, such as glass fibers and polymers, are well known. See, for example, Hermanson, 1996, cited above, and Danczyk et al., 2003.

In one exemplary procedure, nitrocellulose laminated onto a Mylar® card is spray-coated with a solution of antibody (e.g. 3 g/L antibody in 0.1M phosphate buffer, pH 7), incubated for one to several hours, washed with buffer at pH 7, and dried at about 50° C. The membrane may then be blocked by treating with, for example, ethanolamine solution, followed by washing, followed by a PVA solution, and then redried.

Figure 3:
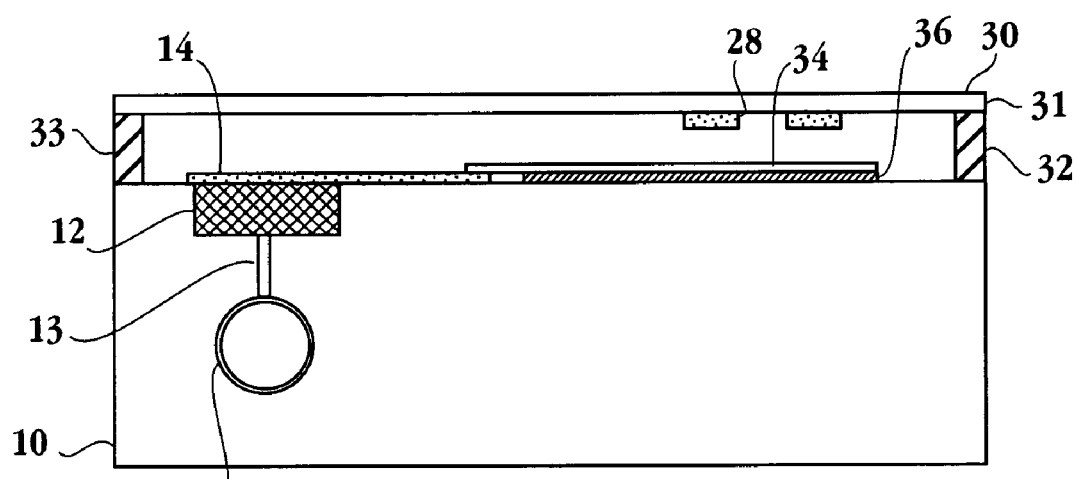
FIG. 3 is a side view of a further embodiment of the assay device, employing an immobilized antibody region.

The application of this variation to the embodiment of FIG. 1A is illustrated in FIG. 3. As shown therein, elements 16 and 20 of FIG. 1A are combined to form a single element 34, containing immobilized antibody (with 18 and 22 combined to form a single support 36). In this case, bridging element 24 (and support 26) are not necessary. Sample would proceed from VLDL precipitation element 14 to element 34 containing immobilized antibody. In a process similar to the transition of FIG. 1B to FIG. 1C, this element, within which HDL is removed from the fluid sample (or a further downstream element into which the sample flows), would then be placed in fluid communication with an LDL test pad, e.g. test pad 28.

In an application of this variation to the embodiment of FIG. 4 (not illustrated), the relative positions of element 34, containing immobilized antibody, and VLDL precipitation element 14 would be reversed. In the later stage of the assay, element 14 (or a further downstream element into which the sample flows) would be placed in fluid communication with an LDL test pad, e.g. test pad 28.

III. Assay Method

The invention provides, in one aspect, a method of directly measuring low-density lipoproteins (LDL) in a blood fluid sample also containing high density lipoproteins (HDL), very low density lipoproteins (VLDL), and/or chylomicrons. The measurement is done entirely in flow strip format by passing the fluid sample through a sequence of porous elements, as described below.

In one embodiment, which employs a device in accordance with the embodiment of FIGS. 1A-C, a blood sample, typically having a volume of about 25-50 µL for a device such as described above, is placed into well 11, and is imbibed through sieving pad 12, where large particulates, including red blood cells, are removed, and thence into VLDL precipitation element 14. Alternatively, as also described above, the sieving function may be performed by element 14, such that pad 12 is optional.

The VLDL precipitation element may be in continuous contact with conjugate pad 16, as shown in FIG. 1A. Preferably, one end (a proximal end) of element 14 is in fluid communication with sample well 11, and the other (a distal end) is in fluid communication with conjugate pad 16. Element 14 contains reagents, as described above, which are effective to precipitate VLDL and chylomicrons and thus remove them from the fluid sample.

In the embodiment of FIGS. 1A-C, the fluid sample then passes into conjugate pad 16, which contains, as described above, a binding agent-antibody conjugate, where the binding agent is preferably biotin and the antibody is preferably anti-apoA1 or anti-apoA2. During a suitable incubation time, which is typically from about 30 seconds to about 5 minutes, prior to contacting conjugate pad 16 with capture zone 20, HDL in the sample binds to the antibody to form, in the preferred embodiment, a biotin-antibody-HDL complex.

After this incubation time, the assay device is adjusted, preferably by moving a reaction bar as shown at 30, to place the conjugate pad 16 in fluid communication with capture zone 20. In the embodiment shown in FIG. 1B, this is done by placing bridging element 24 in simultaneous contact with both elements. Alternatively, the assay device could be designed such that the conjugate pad and capture zone were placed in direct contact at this stage of the assay.

As shown in FIG. 1B, the conjugate pad 16 is in fluid communication with capture zone 20 before the capture zone is placed in fluid communication with test pad 28. During this stage, which is typically from about 1 to 3 minutes, binding agent (e.g. biotin)-antibody-HDL complex is captured by binding to capture agent (e.g. avidin) in capture zone 20, thus removing HDL from the fluid sample. Preferably, at least 90% of the HDL present in the initial blood fluid sample is removed.

In an alternative design, as described above and illustrated in FIG. 3, the anti-HDL antibody can be immobilized to a capture zone, rather than employed in soluble form. Accordingly, sample proceeds directly from the VLDL precipitation element 14 to element 34 containing immobilized antibody. After a suitable incubation time, the assay proceeds to the next stage.

In the next stage, e.g. as illustrated in FIG. 1C, the assay device is adjusted further, preferably by moving a reaction bar as shown at 30, to place the capture zone 20 or 34 (or a further downstream element into which sample flows from the capture zone) in fluid communication with test pad 28. In this position, sample fluid is drawn into the test pad by capillary flow. The two elements are held in fluid communication, e.g. by holding the reaction bar at this position, until a desired degree of wetting of the test pad is achieved. The fluid communication between the capture zone and the test pad is discontinued, if desired, when a desired amount of sample fluid has entered the test pad, and/or after an appropriate contact time, which may be, for example, a designated time between 3 and 20 seconds. This can be done, for example, by moving the reaction bar 30, in the embodiment of FIGS. 1A-C.

As described above, the LDL test pad contains reagents for quantification of LDL-associated cholesterol which produce a detectable response at the top surface of the test pad. The response is detected and used to determine LDL concentration according to standard methods.

In accordance with another alternative design of the device, as described above and exemplified by FIG. 4, the method may be carried out by first removing VLDL/chylomicrons from the sample, followed by removal of HDL, and subsequently passing the sample into an LDL test pad, in which LDL concentration is measured. In this embodiment, the blood sample is placed into a sample loading area, and is imbibed, either directly or through a sieving pad, into conjugate pad 16 (FIG. 4). As above, following a suitable incubation time, the assay device is adjusted to place the conjugate pad in fluid communication with capture zone 20, e.g. by moving a reaction bar as shown at 30 such that bridging element 24 contacts both regions.

Within capture zone 20, binding agent (e.g. biotin)-antibody-HDL complex is captured by binding to capture agent (e.g. avidin), thus removing HDL from the fluid sample. Preferably, at least 90% of the HDL present in the initial blood fluid sample is removed.

The fluid sample then proceeds into precipitation element 14, which is or can be placed in fluid communication with capture zone 20. Following a suitable incubation time if desired, the assay device is adjusted further, preferably by moving a reaction bar as shown at 30, to place the precipitation element 14 (or a further downstream element into which sample flows from 14) in fluid communication with test pad 28.

In this position, sample fluid is drawn into test pad 28 by capillary flow. The two elements are held in fluid communication, e.g. by holding the reaction bar at this position, until a desired degree of wetting of the test pad is achieved. The fluid communication between precipitation element 14 and the test pad is discontinued, if desired, when a desired amount of sample fluid has entered the test pad, and/or after an appropriate contact time, which may be, for example, a designated time between 3 and 20 seconds. This can be done, for example, by moving the reaction bar 30 to separate these elements.

As described above, the LDL test pad contains reagents for quantification of LDL-associated cholesterol which produce a detectable response at the top surface of the test pad. The response is detected and used to determine LDL concentration according to standard methods.

It is claimed:

1. An assay device for the direct measurement of low-density lipoproteins (LDL) in a blood fluid sample also containing high density lipoproteins (HDL), very low density lipoproteins (VLDL), and/or chylomicrons, the device comprising:
    (a) a sample loading area;
    (b) a plurality of porous elements through which said blood fluid sample can flow in sequence by capillary action and/or gravity, wherein adjacent elements are or can be placed in fluid communication with each other, said plurality comprising:
        (1) a VLDL/chylomicron precipitation element, containing reagents effective to selectively precipitate VLDL and chylomicrons in said sample, and composed of a material effective to remove such precipitated VLDL and chylomicrons from said sample;
        (2) an antibody element, containing an antibody effective to specifically bind HDL, thereby forming an HDL-antibody complex;
        (3) a capture zone, wherein said HDL-antibody complex can be bound and thereby removed from said fluid sample; and
        (4) an LDL test pad, downstream of said capture zone and said precipitation element, in which LDL concentration can be assayed, wherein said precipitation element is upstream of said antibody element or downstream of said capture zone; and
    (c) a mounting element effective to adjust the relative positions of said porous elements in such a way as to bring elements into or out of fluid communication with each other.

2. An assay device for the direct measurement of low-density lipoproteins (LDL) in a blood fluid sample also containing high density lipoproteins (HDL), very low density lipoproteins (VLDL), and/or chylomicrons, the device comprising:
    (a) a sample loading area;
    (b) a plurality of porous elements through which said blood fluid sample can flow in sequence by capillary action and/or gravity, wherein adjacent elements are or can be placed in fluid communication with each other, said plurality comprising:
        (1) a VLDL/chylomicron precipitation element, containing reagents effective to selectively precipitate VLDL and chylomicrons in said sample, and composed of a material effective to remove such precipitated VLDL and chylomicrons from said sample;
        (2) an antibody element, containing an antibody effective to specifically bind HDL, thereby forming an HDL-antibody complex, wherein said antibody element contains, in soluble form, a binding agent;
        (3) a capture zone, wherein said HDL-antibody complex can be bound and thereby removed from said fluid sample, wherein said capture zone contains an immobilized capture agent, effective to bind said binding agent; and
        (4) an LDL test pad, downstream of said capture zone and said precipitation element, in which LDL concentration can be assayed, wherein said precipitation element is upstream of said antibody element or downstream of said capture zone; and
    (c) a mounting element effective to adjust the relative positions of said porous elements in such a way as to bring elements into or out of fluid communication with each other.

3. An assay device for the direct measurement of low-density lipoproteins (LDL) in a blood fluid sample also containing high density lipoproteins (HDL), very low density lipoproteins (VLDL), and/or chylomicrons, the device comprising:

(a) a sample loading area;

(b) a plurality of porous elements through which said blood fluid sample can flow in sequence by capillary action and/or gravity, wherein adjacent elements are or can be placed in fluid communication with each other, said plurality comprising:

(1) a VLDL/chylomicron precipitation element, containing reagents effective to selectively precipitate VLDL and chylomicrons in said sample, and composed of a (2) material effective to remove such precipitated VLDL and chylomicrons from said sample;

(3) an antibody element, containing an antibody effective to specifically bind HDL, thereby forming an HDL-antibody complex, wherein said antibody element contains, in soluble form, a biotin;

(4) a capture zone, wherein said HDL-antibody complex can be bound and thereby removed from said fluid sample, wherein said capture zone contains an immobilized avidin or streptavidin, effective to bind said biotin; and (5) an LDL test pad, downstream of said capture zone and said precipitation element, in which LDL concentration can be assayed, wherein said precipitation element is upstream of said antibody element or downstream of said capture zone; and (c) a mounting element effective to adjust the relative positions of said porous elements in such a way as to bring elements into or out of fluid communication with each other.

4. An assay device for the direct measurement of low-density lipoproteins (LDL) in a blood fluid sample also containing high density lipoproteins (HDL), very low density lipoproteins (VLDL), and/or chylomicrons, the device comprising:

(a) a sample loading area;

(b) a plurality of porous elements through which said blood fluid sample can flow in sequence by capillary action and/or gravity, wherein adjacent elements are or can be placed in fluid communication with each other, said plurality comprising:

(1) a VLDL/chylomicron precipitation element, containing reagents effective to selectively precipitate VLDL and chylomicrons in said sample, and composed of a material effective to remove such precipitated VLDL and chylomicrons from said sample;

(2) an antibody element, containing an antibody effective to specifically bind HDL, thereby forming an HDL-antibody complex, wherein said antibody element contains, in soluble form, a binding agent;

(3) a capture zone, wherein said HDL-antibody complex can be bound and thereby removed from said fluid sample, wherein said capture zone contains an immobilized capture agent, effective to bind said binding agent; and (4) an LDL test pad, downstream of said capture zone and said precipitation element, in which LDL concentration can be assayed; wherein said precipitation element is upstream of said antibody element or downstream of said capture zone; and (c) a mounting element effective to adjust the relative positions of said porous elements in such a way as to bring elements into or out of fluid communication with each other, wherein said mounting element is effective to bring said antibody element into fluid communication with said capture zone.

5. An assay device for the direct measurement of low-density lipoproteins (LDL) in a blood fluid sample also containing high density lipoproteins (HDL), very low density lipoproteins (VLDL), and/or chylomicrons, the device comprising:

(a) a sample loading area;

(b) a plurality of porous elements through which said blood fluid sample can flow in sequence by capillary action and/or gravity, wherein adjacent elements are or can be placed in fluid communication with each other, said plurality comprising:

(1) a VLDL/chylomicron precipitation element, containing reagents effective to selectively precipitate VLDL and chylomicrons in said sample, and composed of a material effective to remove such precipitated VLDL and chylomicrons from said sample;

(2) an antibody element, containing an antibody effective to specifically bind HDL, thereby forming an HDL-antibody complex, wherein said antibody element contains, in soluble form, a binding agent;

(3) a capture zone, wherein said HDL-antibody complex can be bound and thereby removed from said fluid sample, wherein said capture zone contains an immobilized capture agent, effective to bind said binding agent;

(4) an LDL test pad, downstream of said capture zone and said precipitation element, in which LDL concentration can be assayed, wherein said precipitation element is upstream of said antibody element or downstream of said capture zone; and (5) a porous bridging element which can be brought into simultaneous contact with said antibody element and said capture zone; and (c) a mounting element effective to adjust the relative positions of said porous elements in such a way as to bring elements into or out of fluid communication with each other, wherein said mounting element is effective to bring said antibody element into fluid communication with said capture zone.

6. An assay device for the direct measurement of low-density lipoproteins (LDL) in a blood fluid sample also containing high density lipoproteins (HDL), very low density lipoproteins (VLDL), and/or chylomicrons, the device comprising:

(a) a sample loading area; and (b) a plurality of porous elements through which said blood fluid sample can flow in sequence by capillary action and/or gravity, wherein adjacent elements are or can be placed in fluid communication with each other, said plurality comprising:

(1) a VLDL/chylomicron precipitation element, containing reagents effective to selectively precipitate VLDL and chylomicrons in said sample, and composed of a material effective to remove such precipitated VLDL and chylomicrons from said sample;

(2) an antibody element, containing an antibody effective to specifically bind HDL, thereby forming an HDL-antibody complex;

(3) a capture zone, wherein said HDL-antibody complex can be bound and thereby removed from said fluid sample; and (4) an LDL test pad, downstream of said capture zone and said precipitation element, in which LDL concentration can be assayed; wherein said precipitation element is upstream of said antibody element or downstream of said capture zone; and (c) a mounting element effective to adjust the relative positions of said porous elements in such a way as to bring elements into or out of fluid communication with each other, wherein said mounting element is effective to bring said LDL test pad into or out of fluid communication with either said capture zone or said precipitation element, whichever is further downstream.

7. An assay device for the direct measurement of low-density lipoproteins (LDL) in a blood fluid sample also containing high density lipoproteins (HDL), very low density lipoproteins (VLDL), and/or chylomicrons, the device comprising:

(a) a sample loading area; and (b) a plurality of porous elements through which said blood fluid sample can flow in sequence by capillary action and/or gravity, wherein adjacent elements are or can be placed in fluid communication with each other, said plurality comprising:

(1) a VLDL/chylomicron precipitation element, containing reagents effective to selectively precipitate VLDL and chylomicrons in said sample, and composed of a material effective to remove such precipitated VLDL and chylomicrons from said sample;

(2) an antibody element, containing an antibody effective to specifically bind HDL, thereby forming an HDL-antibody complex;

(3) a capture zone, wherein said HDL-antibody complex can be bound and thereby removed from said fluid sample; and (4) an LDL test pad, downstream of said capture zone and said precipitation element, in which LDL concentration can be assayed; wherein said precipitation element is upstream of said antibody element or downstream of said capture zone;

(c) a mounting element effective to adjust the relative positions of said porous elements in such a way as to bring elements into or out of fluid communication with each other, wherein said mounting element is effective to bring said LDL test pad into or out of fluid communication with either said capture zone or said precipitation element, whichever is further downstream; and (d) a reaction bar to which said LDL test pad is attached.

* * * * *